US012692520B2

(12) United States Patent
Wang et al.

(10) Patent No.: US 12,692,520 B2
(45) Date of Patent: Jul. 28, 2026

(54) METHOD FOR EFFICIENTLY PRODUCING LACTIC ACID BY FERMENTING BREWERS' SPENT GRAINS

(71) Applicants: Chengdu Environmental Investment Group Co., Ltd, Chengdu (CN); Chengdu Xingrong Renewable Energy Co., Ltd, Chengdu (CN)

(72) Inventors: Ying Wang, Chengdu (CN); Yi Rao, Chengdu (CN); Ming Gao, Chengdu (CN); Chunjiang Yu, Chengdu (CN); Lijuan Zhong, Chengdu (CN)

(73) Assignees: Chengdu Environmental Investment Group Co., Ltd, Chengdu (CN); Chengdu Xingrong Renewable Energy Co., Ltd, Chengdu (CN)

( * ) Notice: Subject to any disclaimer, the term of this patent is extended or adjusted under 35 U.S.C. 154(b) by 254 days.

(21) Appl. No.: 18/638,698

(22) Filed: Apr. 18, 2024

(65) Prior Publication Data

US 2025/0051809 A1     Feb. 13, 2025

(30) Foreign Application Priority Data

Aug. 9, 2023     (CN) ......................... 202310994030.8

(51) Int. Cl.
| | |
|---|---|
| *C12P 7/56* | (2006.01) |
| *C12N 1/20* | (2026.01) |
| *C12N 1/22* | (2006.01) |
| *C12R 1/00* | (2006.01) |

(52) U.S. Cl.
CPC ................. *C12P 7/56* (2013.01); *C12N 1/20* (2013.01); *C12N 1/22* (2013.01); *C12Y* *302/01004* (2013.01); *C12P 2201/00* (2013.01); *C12R 2001/00* (2021.05)

(58) Field of Classification Search
None
See application file for complete search history.

(56) References Cited

U.S. PATENT DOCUMENTS

| | | | | |
|---|---|---|---|---|
| 8,962,286 | B2 * | 2/2015 | Milos | C12N 9/2437 |
| | | | | 435/162 |
| 2007/0037259 | A1 * | 2/2007 | Hennessey | C12M 27/02 |
| | | | | 435/161 |
| 2013/0330791 | A1 * | 12/2013 | Milos | C12P 7/14 |
| | | | | 435/162 |
| 2015/0259633 | A1 * | 9/2015 | Milos | C12P 7/06 |
| | | | | 435/200 |
| 2019/0070230 | A1 * | 3/2019 | Honma | A61K 35/74 |
| 2019/0200640 | A1 * | 7/2019 | Gil-Martinez | C12C 5/006 |

* cited by examiner

*Primary Examiner* — Blaine Lankford

(57) ABSTRACT

The present disclosure relates to a method for efficiently producing lactic acid by fermenting brewers' spent grains. The method specifically includes the following steps: (1) adding water to brewers' spent grains after alkali pretreatment so as to adjust a solid content of a fermentation production system to 10%-15%, adding cellulase to the brewers' spent grains according to an addition amount of 5 FPU/g-10 FPU/g, carrying out hydrolysis at 50° C.-60° C. and pH of 4.5-5.2 for 20 hours-48 hours, and obtaining a prehydrolyzed substrate; and (2) inoculating hydrolysate prepared in step (1) with a lactic acid bacteria seed solution with a viable count of $1\times10^8$ CFU/mL-$1\times10^{10}$ CFU/mL according to an inoculation amount of 10%-15% (v/v), conducting fermentation at 40° C.-55° C. and pH of 6.0-7.2 for 72 hours-96 hours, and obtaining a fermentation broth.

12 Claims, 3 Drawing Sheets

METHOD FOR EFFICIENTLY PRODUCING LACTIC ACID BY FERMENTING BREWERS' SPENT GRAINS

TECHNICAL FIELD

The present disclosure relates to the technical field of biomass waste recycling, and particularly relates to a method for efficiently producing lactic acid by fermenting brewers' spent grains.

BACKGROUND

Brewers' spent grains (BSGs) are waste biomass materials produced when industrial production is carried out with barley, and include residues from industrial brewing, beverage processing and food production processes and processing residues. At present, each time 100 L of beer is produced, about 20 Kg of BSGs will be generated as a by-product. It is estimated that over 30 million tons of waste BSGs are produced annually in the world. This number is expected to further increase with vigorous development of the micro-brewery market. Currently, most BSGs are directly discarded into landfills or used as animal feed. The BSGs include rich insoluble fibers, such as a husk, a seed coat and pericarp. They further include storage proteins of endosperm cells. These two kinds of components account for about 70% and 20% of the BSGs, respectively. A fiber is mainly composed of cellulose, hemicellulose (that is, arabinoxylan), and lignin. Because of a high carbohydrate content (up to 50% in dry weight), the BSG waste biomass material is conducive to biofermentation production processes of energy and biofuel, biogas, antibiotics, enzyme preparations and some important organic acids, etc. It is a lignocellulosic biomass material with great potential and can be used for bioconversion production of various high value-added platform chemicals.

In the existing research, lactic acid is prepared with the BSGs. This method still has technical bottlenecks. First, it needs to add exogenous nutrients such as a nitrogen source, metal ions and trace elements, and additionally needs to add β-glucosidase so as to maintain high substrate hydrolysis efficiency, which leads to higher cost. Second, an existing BSG fermentation method mainly uses a synchronous hydrolysis and saccharification mode, and an initial fermentable sugar concentration in this system is too low, resulting in slow growth and metabolism of lactic acid bacteria, which is not conducive to lactic acid biotransformation. Third, a hydrolysis product of the BSGs is not only composed of hexose (for instance, glucose and cellobiose), but also releases pentose (for instance, xylose and arabinose) equal to the hexose in concentration, and the hexose such as glucose, an optional carbon source, is preferentially used by the lactic acid bacteria and inhibits catabolism of other sugars such as the pentose, such that lactic acid production is delayed, fermentation time is long, and a production rate and yield are low. Therefore, it is necessary to study a more efficient and economical BSG lactic acid fermentation method.

SUMMARY

An objective of the present disclosure is to provide a method for efficiently producing lactic acid by fermenting brewers' spent grains. The method specifically includes the following steps:

(1) adding water to brewers' spent grains after alkali pretreatment so as to adjust a solid content of a fermentation production system to 10%-15%, adding cellulase into the brewers' spent grains according to an addition amount of 5 FPU/g-10 FPU/g, carrying out hydrolysis at 50° C.-60° C. and pH of 4.5-5.2 for 20 hours-48 hours, and obtaining a prehydrolyzed substrate; and (2) inoculating hydrolysate prepared in step (1) with a lactic acid bacteria seed solution with a viable count of $1\times10^8$ CFU/mL-$1\times10^{10}$ CFU/mL according to an inoculation amount of 10%-15% (v/v), fermenting at 40° C.-55° C. and pH of 6.0-7.2 for 72 hours-96 hours, and obtaining a fermentation broth.

In an optional technical solution of the present disclosure, the brewers' spent grains are waste biomass materials produced when industrial production is carried out with barley, and include residues from industrial brewing, beverage processing and food production processes and processing residues.

In an optional technical solution of the present disclosure, a cellulose content of the brewers' spent grains after the alkali pretreatment is 15%-30% of a brewers' spent grain dry basis and a hemicellulose content of the brewers' spent grains after the alkali pretreatment is 20%-40% of the brewers' spent grain dry basis.

In an optional technical solution of the present disclosure, in step (1), a method for preparing the brewers' spent grains after alkali pretreatment includes: adding an alkaline solution having a concentration of 0.5 wt %-3.0 wt % to the brewers' spent grains according to a solid-liquid weight ratio of 1:5-1:10, carrying out cooking at 100° C.-120° C. for 10 min-20 min, carrying out solid-liquid separation, obtaining and washing solid residues to a neutral state, and obtaining the brewers' spent grains.

In an optional technical solution of the present disclosure, the alkaline solution is either or a combination of NaOH and KOH.

In an optional technical solution of the present disclosure, in step (2), a method for preparing the lactic acid bacteria seed solution includes: transferring *Enterococcus mundtii* China General Microbiological Culture Collection Center (CGMCC) 22227 glycerol-frozen bacteria into a deMan-Rogosa-Sharpe (MRS) culture medium, incubating for 24 hours-48 hours to obtain an activated seed solution, then transferring the activated seed solution into a modified MRS (mMRS) culture medium according to an inoculation amount of 10%-15%, carrying out an anaerobic culture at 40° C.-45° C. for 8 hours-12 hours, and obtaining the lactic acid bacteria seed solution with a viable count of $1\times10^8$ CFU/mL-$1\times10^{10}$ CFU/mL.

In an optional technical solution of the present disclosure, the mMRS culture medium includes the components as follows: each liter of deionized water contains 10 g of peptone, 8 g of beer extract, 5 g of $CH_3COONa\cdot3H_2O$, 4 g of yeast extract, 2 g of $K_2HPO_4$, 2 g of ammonium citrate, 0.2 g of $MgSO_4\cdot7H_2O$, 0.05 g of $MnSO_4\cdot4H_2O$, 1 mL Tween 80, 10 g of cellobiose and 10 g of xylose. An initial pH value is adjusted to 7.0, and sterilization is carried out at 115° C. for 15 min.

In an optional technical solution of the present disclosure, in step (2), a fermentation temperature is 40° C.-45° C.

In an optional technical solution of the present disclosure, a lactic acid concentration of the fermentation broth is not smaller than 45 g/L, and optionally not smaller than 50 g/L.

In an optional technical solution of the present disclosure, a lactic acid conversion rate of substrate fermentable sugar is not smaller than 0.60 g/g, and optionally not smaller than 0.7 g/g.

In an optional technical solution of the present disclosure, a lactic acid production rate is not smaller than 3.0 g/h/L, and optionally not smaller than 3.5 g/h/L.

In an optional technical solution of the present disclosure, an acetic acid concentration of the fermentation broth is smaller than 2.0 g/L, and optionally smaller than 1.3 g/L.

In an optional technical solution of the present disclosure, a lactic acid yield obtained through unit enzyme preparation addition is greater than 9 (g-Lac/FPU), and optionally greater than 10 (g-Lac/FPU).

Unless otherwise specified, when the present disclosure relates to a percentage between liquids, the percentage is a volume/volume percentage; when the present disclosure relates to a percentage between liquid and solid, the percentage is a volume/weight percentage; and when the present disclosure relates to a percentage between solid and liquid, the percentage is a weight/volume percentage. Percentages in other cases are all weight/weight percentages.

Unless otherwise specified, the present disclosure detects a fermentation product content through the following method:

(1) Concentrations of lactic acid and acetic acid are measured through high performance liquid chromatography, a sample is separated with a Shodex Sugar SH1011 liquid chromatography column (8.0 mm×300 mm), and then detection is carried out with a differential refractive index detector (RID). Chromatographic conditions include: a column temperature of 60° C.; a mobile phase of 5 mM $H_2SO_4$; a flow rate of 1.0 mL/min; and an injection volume of 10 μL.

(2) Lactic acid conversion rate of substrate fermentable sugar=maximum lactic acid concentration/total sugar concentration.

The total sugar concentration is determined through a phenol-sulfuric acid method. Firstly, a standard curve is made with standard glucose. Specifically, 10 mg of standard glucose is accurately weighed in a 250 mL volumetric flask, water is added to a scale, 0.1 mL, 0.2 mL, 0.3 mL, 0.4 mL, 0.5 mL, 0.6 mL, 0.8 mL and 1.0 ml of water are absorbed separately, then supplementation is carried out to 1.0 mL with distilled water, then 1.0 mL of 5% phenol solution and 5.0 mL of concentrated sulfuric acid are added, shaking and cooling are carried out, the obtained solution is placed at a room temperature for 20 min, and an optical density of the solution is measured at 490 nm. 1.0 mL of water subjected the same color rendering operation is used as a blank control. Abscissae represent a microgram number of total sugar, and ordinates represent an optical density value. In this way, a standard curve is obtained. A sample is processed through operations consistent with the above operations, and a total sugar content of the sample is finally obtained according to the standard curve.

(3) Lactic acid production rate=lactic acid concentration variation during fermentation/fermentation time (4) Lactic acid yield obtained through unit enzyme preparation addition=maximum lactic acid concentration/cellulose addition amount (5) Contents of cellulose and hemicellulose are quantitatively analyzed through a National Renewable Energy Laboratory (NREL) method.

Compared with the prior art, the present invention has the beneficial effects:

1. According to the present disclosure, the brewers' spent grains after alkali pretreatment are used as a raw material, and only low-content cellulase is added for prehydrolysis, such that 50% or above of cellulose in the raw material is converted into glucose and cellobiose during prehydrolysis; and then the lactic acid bacteria are directly inoculated for synchronous fermentation, such that feedback inhibition in an enzymolysis process is avoided, the lactic acid conversion rate of the substrate is improved, synchronous lactic acid biotransformation of xylose and a mixed substrate of arabinose (pentose), glucose (hexose) and cellobiose is achieved, and the lactic acid production rate is enhanced.

2. According to the present disclosure, β-glucosidase and other nutrients do not need to be added, a commercial cellulase dosage is low, and the lactic acid production rate and conversion rate are high. Compared with a conventional lactic acid production method of pretreatment-enzymolysis and saccharification-fermentation, production cost of the present disclosure is reduced by 20%-40%, such that a new way is provided for cheap industrial production of lactic acid.

3. The present disclosure is simple in process, low in cost, and environmentally friendly, and can achieve industrial production.

4. According to the present disclosure, feedback inhibition in an enzymolysis process is avoided, the lactic acid conversion rate of the substrate is improved, synchronous lactic acid biotransformation of xylose and a mixed substrate of arabinose (pentose), glucose (hexose) and cellobiose is achieved, and the lactic acid production rate is enhanced. 53.1 g/L optically pure L-lactic acid is achieved, and a maximum volume yield is 3.65 g/L/h, such that lactic acid production potential of a lignocellulose substrate can be greatly improved.

DETAILED DESCRIPTION OF THE EMBODIMENTS

Embodiments of the present disclosure will be further described in detail below in combination with examples. The following examples are used for illustrating the present disclosure, instead of limiting the scope of the present disclosure.

The Brewers' spent grains (BSGs) include rich insoluble fibers, such as a husk, a seed coat and pericarp. They further include storage proteins of endosperm cells. These two kinds of components account for about 70% and 20% of the BSGs, respectively. The rest of BSGs is ash. A fiber is mainly composed of cellulose, hemicellulose (that is, arabinoxylan), and lignin. BSG solids subjected to proper alkaline pretreatment contain no harmful substances that have obvious inhibitory effects on cellulase hydrolysis and lactic acid fermentation, and thus are better raw materials for lactic acid production.

Figure 1:
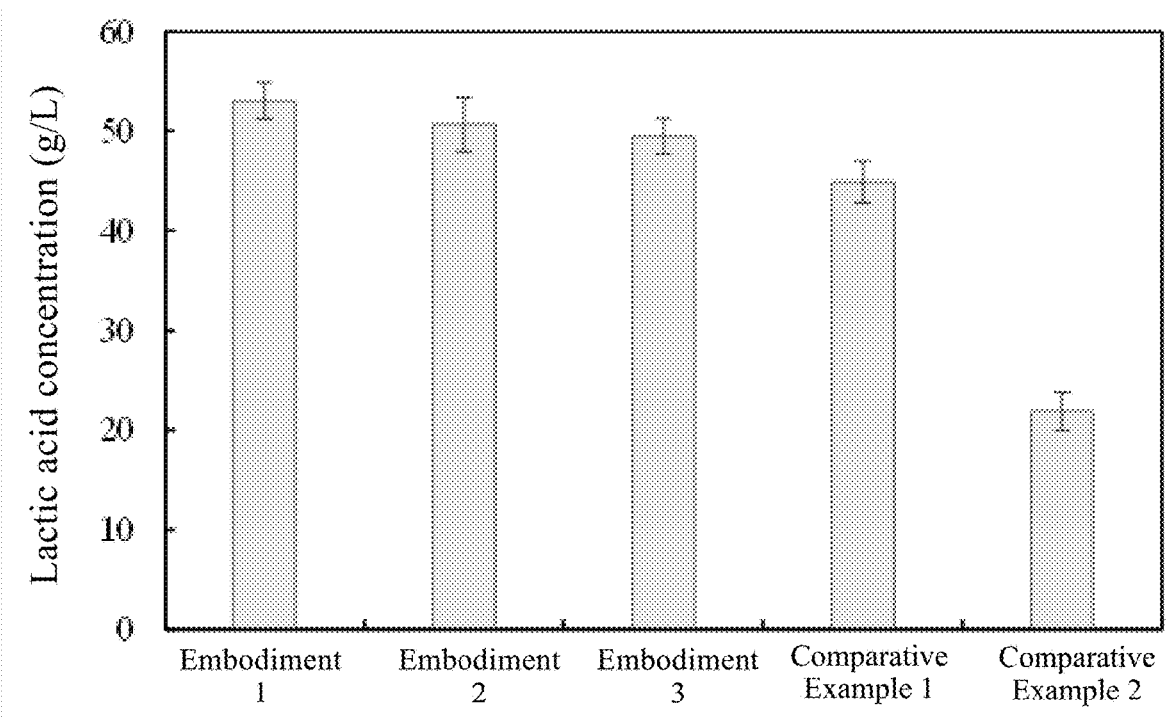
FIG. 1 shows a comparison between lactic acid yields of fermentation broths of Embodiments 1-3 and Comparative Examples 1-2.
Figure 2:
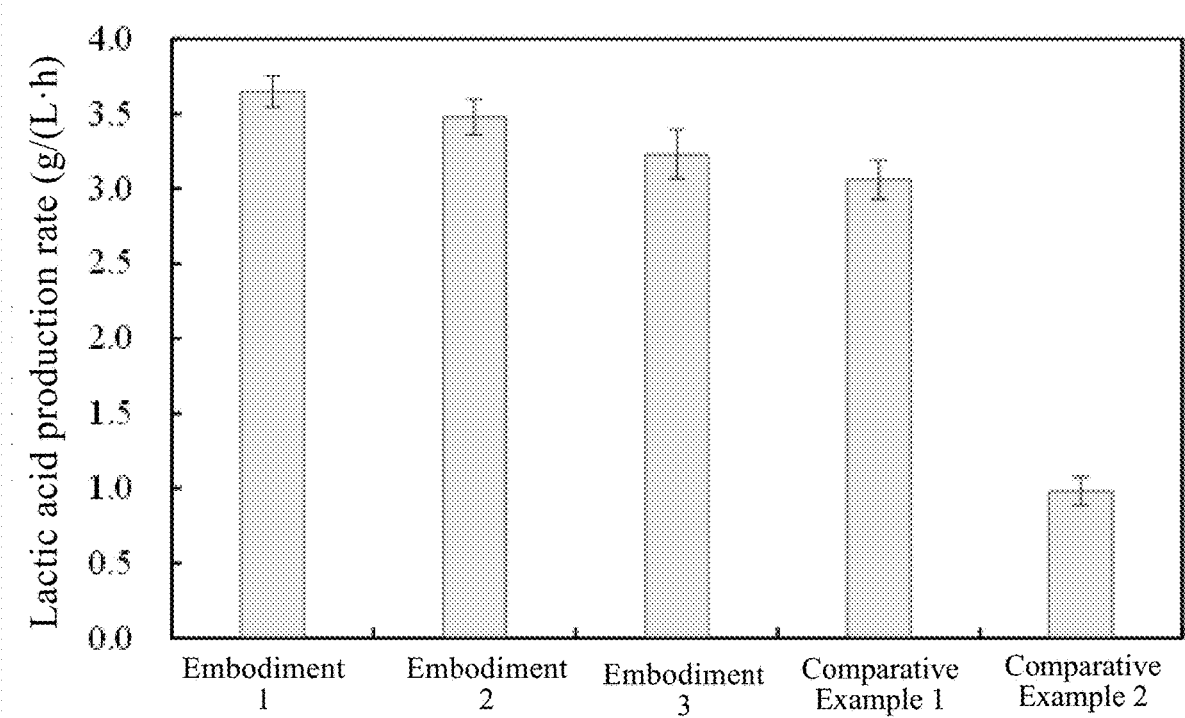
FIG. 2 shows a comparison between lactic acid production rates of fermentation broths of Embodiments 1-3 and Comparative Examples 1-2.
Figure 3:
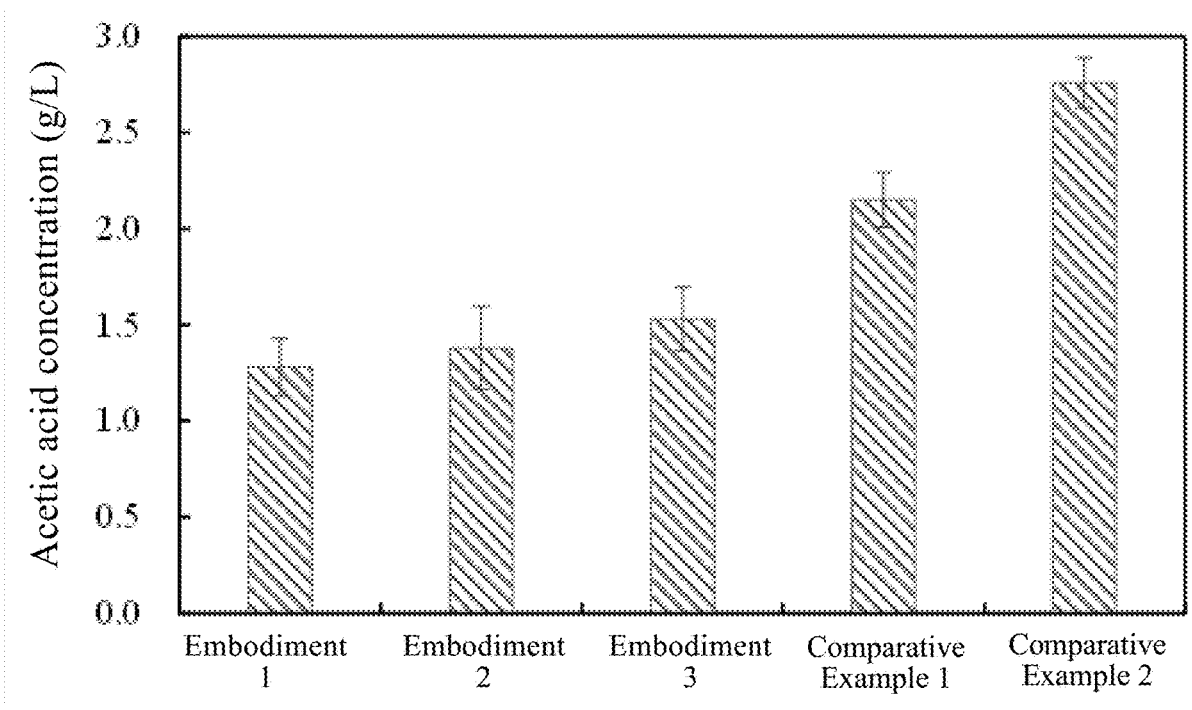
FIG. 3 shows a comparison between acetic acid concentrations of fermentation broths of Embodiments 1-3 and Comparative Examples 1-2.
Figure 4:
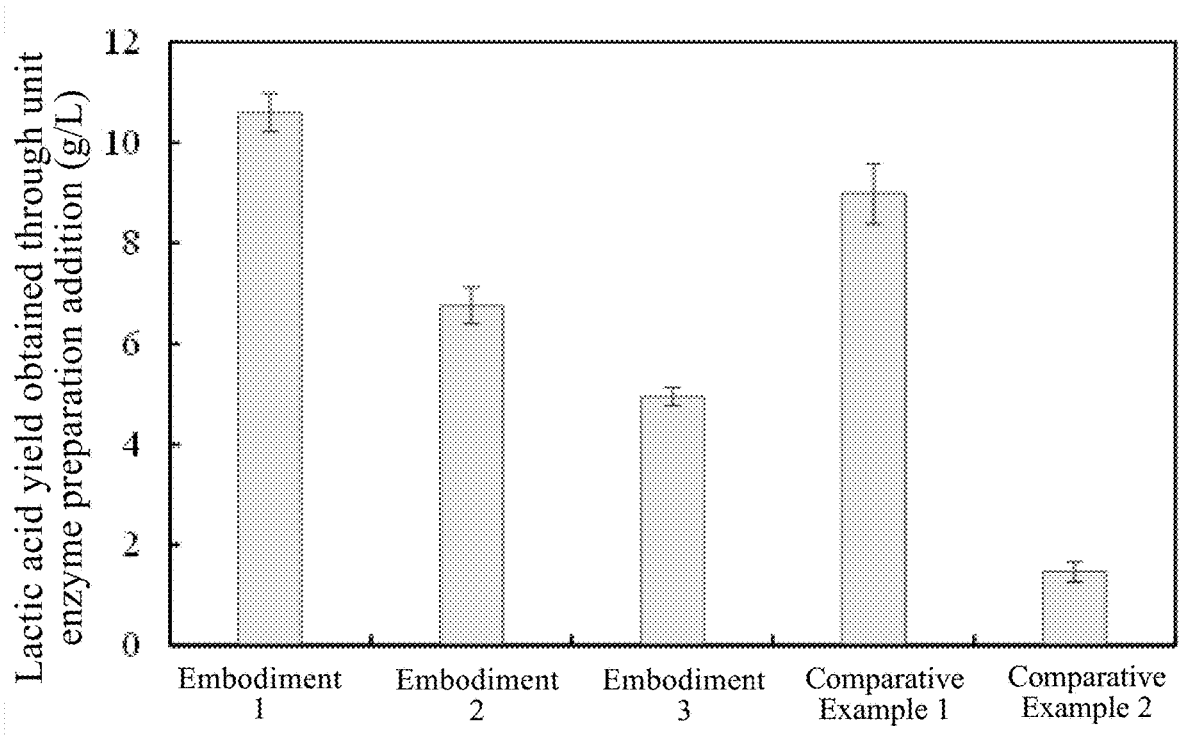
FIG. 4 shows a comparison between lactic acid yields obtained through unit enzyme preparation addition in Embodiments 1-3 and Comparative Examples 1-2.
Figure 5:
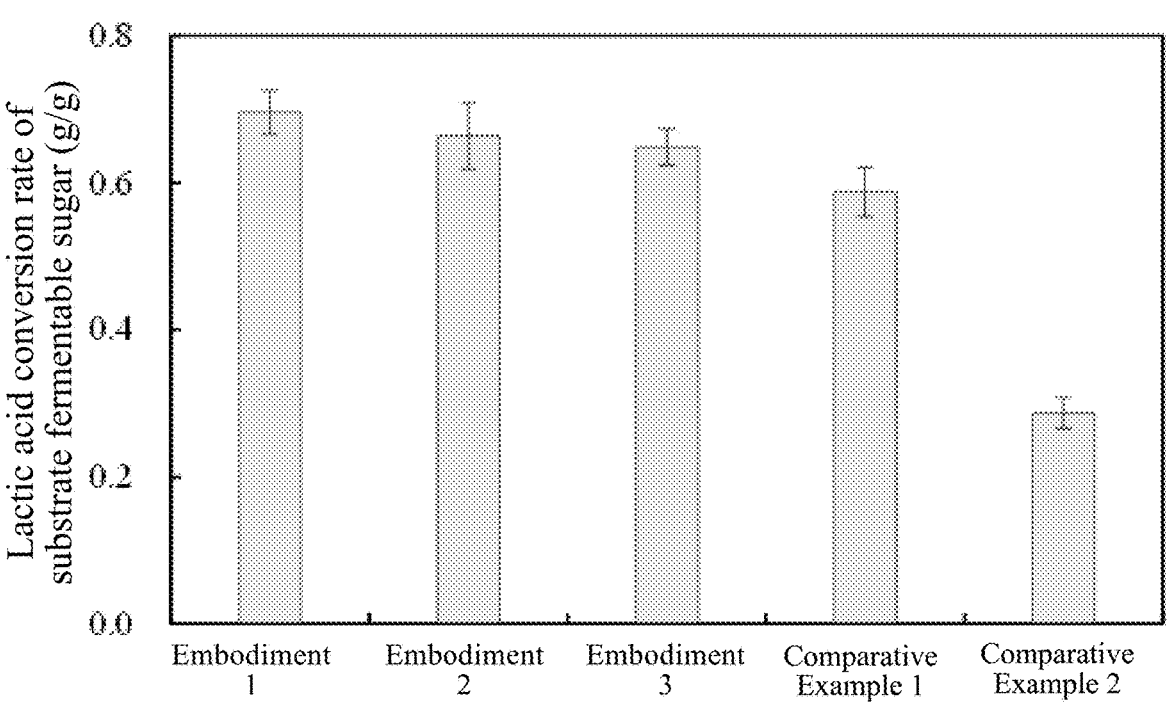
FIG. 5 shows a comparison between lactic acid conversion rates of substrate fermentable sugars of Embodiments 1-3 and Comparative Examples 1-2.
Figure 6:
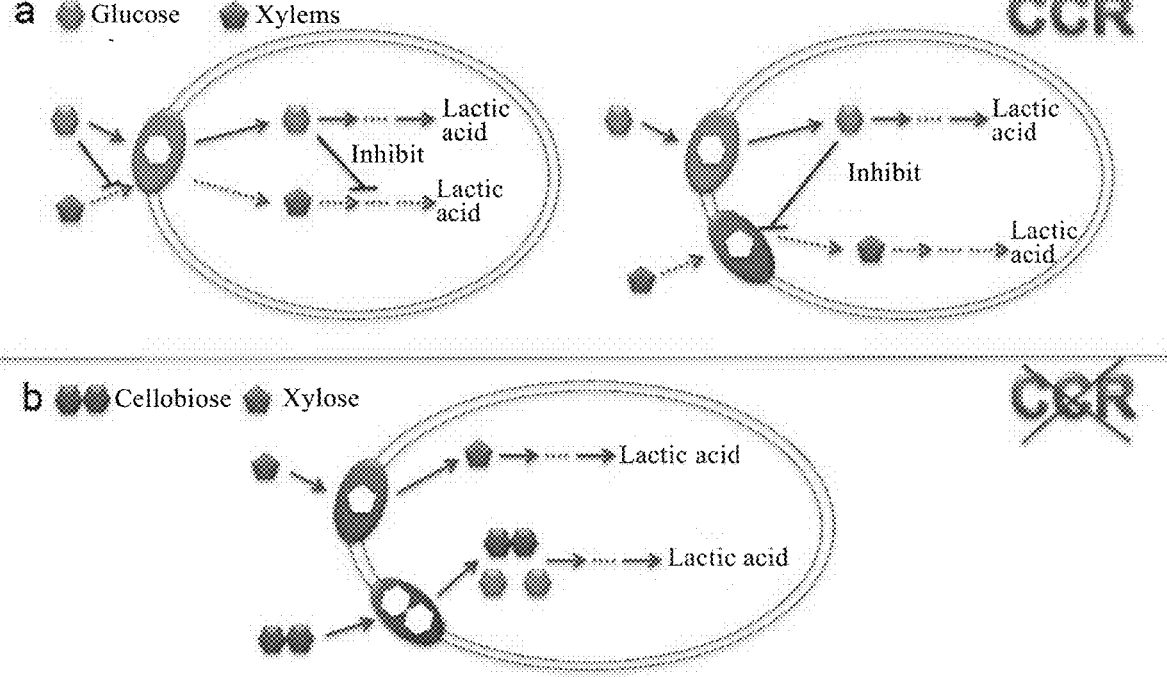
FIG. 6 is a flow diagram of carbon catabolite repression (CCR) of glucose of the present disclosure and a breakthrough mechanism of the present disclosure.

According to a conventional fermentation method with hydrolysis and saccharification, lactic acid fermentation can be implemented only after cellulose is hydrolyzed into glucose. However, hydrolysis products of the BSGs are not only composed of hexoses (such as glucose), but also release pentoses (such as xylose and arabinose) having the same concentration. In the presence of mixed sugar substrates, the hexoses such as glucose are preferentially used by lactic acid bacteria as a preferred carbon source, and catabolism of other sugars such as pentoses is inhibited. The phenomenon is called carbon catabolite repression (CCR) of glucose (as shown in zone a in FIG. 6), which leads to delayed lactic acid production, long fermentation time, and low production rate and yield.

Waste brewers' spent grains (having a water content of 60%-70%) are taken from a brewery, and then a NaOH alkaline solution having a concentration of 1.0 wt % is added. A solid-liquid weight ratio is adjusted to 1:10, and mixing is carried out uniformly. Cooking is carried out at 120° C. for 15 min. After solid-liquid separation, liquid is discarded, and solid residues are washed to a neutral state, such that the brewers' spent grains after alkali pretreatment are obtained. After detection, a brewers' spent grain dry basis after alkali pretreatment contains 18.2% of cellulose and 20.4% of hemicellulose.

Lactic acid bacteria used are *Enterococcus mundtii* China General Microbiological Culture Collection Center (CGMCC) 22227. The lactic acid bacteria seed solution is cultured through the following steps: 1 mL of *Enterococcus mundtii* CGMCC 22227 glycerol-frozen bacteria are transferred into a 9 mL modified deMan-Rogosa-Sharpe (mMRS) culture medium, incubation is carried out at 43° C. for 24 hours, an activated seed solution is obtained, then 10 mL of activated seed solution is transferred into a 90 mL mMRS culture medium, an anaerobic culture is carried out at 43° C. for 8 hours, and the lactic acid bacteria seed solution with a viable count of $3.7 \times 10$ CFU/mL is obtained.

The mMRS culture medium is as follows: each liter of deionized water includes the following components of 10 g of peptone, 8 g of beer extract, 5 g of $CH_3COONa \cdot 3H_2O$, 4 g of yeast extract, 2 g of $K_2HPO_4$, 2 g of ammonium citrate, 0.2 g of $MgSO_4 \cdot 7H_2O$, 0.05 g of $MnSO_4 \cdot 4H_2O$, 1 mL Tween 80, 10 g of cellobiose and 10 g of xylose. An initial pH value is adjusted to 7.0, and sterilization is carried out at 115° C. for 15 min.

The cellulase is a commercially available enzyme having an enzyme activity of 60 FPU/mL.

In the above description, a strain *Enterococcus mundtii* CGMCC22227 related to the technical content of the present disclosure is provided by a second inventor, Dr. Gao Ming (who is a founder of the Beijing Yingbohui Environmental Protection Technology Co., Ltd.). The strain is extracted from goat feces by Dr. Gao Ming, an entire gene map of the strain is detected, and a preservation certificate of the strain is provided in 2021 (with reference to Annex 4 for the preservation certificate). The strain is disclosed in the previous patent application CN114369627B of Dr. Gao Ming (an applicant is University of Science and Technology Beijing, and Gao Ming is one of the inventors) for lactic acid fermentation, and belongs to known bacteria (with reference to Annex 5). However, after the follow-up research of Dr. Gao Ming, it is found that the strain had an ability to biotransform xylose and glucose simultaneously, especially two carbon sources metabolized by the strain can conduct homolactic fermentation (no by-product is generated in a metabolic pathway), and the strain has an efficient treatment effect on lignocellulose. Therefore, Dr. Gao Ming uses the strain in lactic acid fermentation of BSG hydrolysates so as to achieve unexpected technical results.

Embodiment 1

A method for efficiently producing lactic acid by fermenting brewers' spent grains according to the present disclosure:

(1) Water is added to 20 g of brewers' spent grains after alkali pretreatment so as to adjust a solid content of a fermentation production system to 10%, cellulase is added into the brewers' spent grains according to an addition amount of 5 FPU/g, hydrolysis is carried out at 50° C. and pH of 5.0 for 20 hours, and a prehydrolyzed substrate is obtained.

(2) A lactic acid bacteria seed solution is added into the pre-hydrolyzed substrate in step (1) according to an inoculation amount of 10% (v/v), fermentation is carried out at 43° C. and pH of 6.0 for 96 hours, and a fermentation broth is obtained.

Embodiment 2

A method for efficiently producing lactic acid by fermenting brewers' spent grains according to the present disclosure:

(1) Water is added to 20 g of brewers' spent grains after alkali pretreatment so as to adjust a solid content of a fermentation production system to 10%, cellulase is added into the brewers' spent grains according to an addition amount of 7.5 FPU/g, hydrolysis is carried out at 50° C. and pH of 5.0 for 30 hours, and a prehydrolyzed substrate is obtained.

(2) a lactic acid bacteria seed solution is added into the pre-hydrolyzed substrate in step (1) according to an inoculation amount of 10% (v/v), fermentation is carried out at 43° C. and pH of 6.0 for 84 hours, and a fermentation broth is obtained.

Embodiment 3

A method for efficiently producing lactic acid by fermenting brewers' spent grains according to the present disclosure:

(1) Water is added to 20 g of brewers' spent grains after alkali pretreatment so as to adjust a solid content of a fermentation production system to 10%, cellulase is added into the brewers' spent grains according to an addition amount of 10 FPU/g, hydrolysis is carried out at 50° C. and pH of 5.0 for 40 hours, and hydrolysate is obtained.

(2) A lactic acid bacteria seed solution is added into the hydrolysate in step (1) according to an inoculation amount of 10% (v/v), fermentation is carried out at 43° C. and pH of 6.0 for 72 hours, and a fermentation broth is obtained.

Comparative Example 1

Water is added to 20 g of brewers' spent grains after alkali pretreatment so as to adjust a solid content of a fermentation production system to 10%, and cellulase is added into the brewers' spent grains according to an addition amount of 5 FPU/g. Meanwhile, a lactic acid bacteria seed solution is added according to an inoculation amount of 10% (v/v), fermentation is carried out at 43° C. and pH of 6.0 for 96 hours, and a fermentation broth is obtained.

Comparative Example 2

(1) Water is added to 20 g of brewers' spent grains after alkali pretreatment so as to adjust a solid content of a fermentation production system to 10%, cellulase is added into the brewers' spent grains according to an addition amount of 15 FPU/g, hydrolysis is carried out at 50° C. and pH of 5.0 for 96 hours, and hydrolysate is obtained.

(2) A lactic acid bacteria seed solution is added into the hydrolysate in step (1) according to an inoculation amount of 10% (v/v), fermentation is carried out at 43° C. and pH of 6.0 for 96 hours, and a lactic acid fermentation broth is obtained.

Concentration variations of lactic acid and acetic acid, lactic acid production rates, lactic acid yields obtained through unit enzyme preparation addition and lactic acid conversion rates of substrate fermentable sugars in fermentation systems in Embodiments 1-3 and Comparative Examples 1-2 are detected as shown in FIGS. 1-5.

Conclusion: the effect are innovatively provided as follows:

1. Orderly and controllable release of glucose and xylose is controlled to greatly alleviate carbon catabolite repression. Through experimental exploration, the applicant finds that an addition amount of cellulase and prehydrolysis time are adjusted without adding β-glucosidase, such that a glucose release amount can be controlled, and a cellobiose content can be increased (cellobiose and pentose can be co-metabolized to produce lactic acid without CCR, as shown in zone b in FIG. 6). In this way, co-metabolism of pentose, hexose and cellobiose can be implemented, and lactic acid can be produced efficiently.

2. Strains having an ability to simultaneously and efficiently biotransform xylose and glucose are screened out, which can be combined with a controllable hydrolysis sugar-release technology of barley malt residues, such that efficient fermentation can be implemented to produce lactic acid.

Finally, Embodiments 1-3 and Comparative Examples 1-2 are set in the application file so as to prove that cellulase hydrolysis conditions, strain growth conditions and lactic acid fermentation conditions (such as a cellulase addition amount, enzymolysis time, and a pH value) in the present disclosure have to be well-matched so as to achieve efficient fermentation, and simultaneous saccharification and hydrolysis (Comparative Example 1) and long hydrolysis time (Comparative Example 2) cannot achieve efficient fermentation, which is not easily conceived by those skilled in the art through simple experiments.

In the above examples, selection of specific data and any raw materials specifically disclosed is not used for limiting the protection scope of the claims. The technical solution of the present disclosure may be completely implemented by selecting any specific numerical value, raw materials, etc. within each numerical range of the claims. Those of ordinary skill in the art may also make some improvements and modifications without departing from the principle of the present disclosure, and these improvements and modifications should also fall within the protection scope of the present disclosure.

What is claimed is:

1. A method for efficiently producing lactic acid by fermenting brewers' spent grains, specifically comprising the following steps:

adding an alkali solution with a concentration of 0.5-3.0 wt % into brewers' spent grains according to a solid-liquid weight ratio of 1:5-1:10, cooking at 100-120° C. for 10-20 min, carrying out a solid-liquid separation, obtaining and washing solid residues to a neutral state, and obtaining alkali-pretreated brewers' spent grains;

adding water to the alkali-pretreated brewers' spent grains so as to adjust a solid content of a fermentation production system to 10%-15%, adding cellulase into the alkali-pretreated brewers' spent grains according to an addition amount of 5 FPU/g-10 FPU/g, carrying out hydrolysis at 50° C.-60° C. and pH of 4.5-5.2 for 20 hours-48 hours, and obtaining a prehydrolyzed substrate; and inoculating the prehydrolyzed substrate with a lactic acid bacteria seed solution with a viable count of $1 \times 10^8$ CFU/mL-$1 \times 10^{11}$ CFU/mL according to an inoculation amount of 10%-15% (v/v), fermenting at 40° C.-55° C. and pH of 6.0-7.2 for 72 hours-96 hours, and obtaining a fermentation broth containing the lactic acid; and wherein a lactic acid concentration of the fermentation broth is not smaller than 45 grams per milliliter (g/L).

2. The method according to claim 1, wherein the brewers' spent grains are waste biomass materials produced when industrial production is carried out with barley, and comprise residues from industrial brewing, beverage processing and food production processes and processing residues.

3. The method according to claim 1, wherein a cellulose content of the alkali-pretreated brewers' spent grains is 15%-30% of a brewers' spent grain dry basis and a hemicellulose content of the alkali-pretreated brewers' spent grains is 20%-40% of the brewers' spent grain dry basis.

4. The method according to claim 1, wherein the lactic acid bacteria seed solution is prepared by the following steps: transferring *Enterococcus mundtii* China General Microbiological Culture Collection Center (CGMCC) 22227 glycerol-frozen bacteria into a deMan-Rogosa-Sharpe (MRS) culture medium, incubating for 24 hours-48 hours to obtain an activated seed solution, then transferring the activated seed solution into a modified MRS (mMRS) culture medium according to an inoculation amount of 10%-15%, carrying out an anaerobic culture at 40° C.-45° C. for 8 hours-12 hours, and obtaining the lactic acid bacteria seed solution with a viable count of $1 \times 10^8$ CFU/mL-$1 \times 10^{10}$ CFU/mL.

5. The method according to claim 1, wherein a lactic acid concentration of the fermentation broth is not smaller than 50 g/L.

6. The method according to claim 1, wherein a lactic acid conversion rate of substrate fermentable sugar is not smaller than 0.60 g/g.

7. The method according to claim 1, wherein a lactic acid production rate is not smaller than 3.0 g/h/L.

8. The method according to claim 1, wherein an acetic acid concentration of the fermentation broth is smaller than 2.0 g/L.

9. The method according to claim 1, wherein a lactic acid yield obtained through unit enzyme preparation addition is greater than 9 grams of lactic acid per filter paper unit (g-Lac/FPU).

10. The method according to claim 4, wherein the modified mMRS culture medium comprises components as follows: each liter of deionized water contains 10 g of peptone, 8 g of beer extract, 5 g of sodium acetate trihydrate (CH$_3$COONa·3H$_2$O), 4 g of yeast extract, 2 g of potassium hydrogen phosphate (K$_2$HPO$_4$), 2 g of ammonium citrate, 0.2 g of magnesium sulfate heptahydrate (MgSO$_4$·H$_2$O), 0.05 g of manganese(II) sulfate tetrahydrate (MnSO$_4$·4H$_2$O), 1 mL Tween 80, 10 g of cellobiose and 10 g of xylose; where an initial pH value is adjusted to 7.0, and sterilization is carried out at 115° C. for 15 min.

11. A method for efficiently producing lactic acid by fermenting brewers' spent grains, comprising the following steps:

adding a NaOH alkali solution with a concentration of 1.0 wt % into brewers' spent grains according to a solid-liquid weight ratio of 1:10, cooking at 120° C. for 15 min, carrying out a solid-liquid separation, obtaining and washing solid residues to a neutral state, and obtaining alkali-pretreated brewers' spent grains;

adding water to 20 g of the alkali-pretreated brewers' spent grains so as to adjust a solid content of a fermentation production system to 10%, adding cellulase into the alkali-pretreated brewers' spent grains according to an addition amount of 5 FPU/g, carrying out hydrolysis at 50° C. and pH of 5.0 for 20 hours, and obtaining a prehydrolyzed substrate;

inoculating the prehydrolyzed substrate with a lactic acid bacteria seed solution with a viable count of 3.7×10$^8$ CFU/mL according to an inoculation amount at a volume ratio of 10%, fermenting at 43° C. and pH of 6.0 for 96 hours, and obtaining a fermentation broth containing the lactic acid; and wherein a dry basis of the alkali-pretreated brewers' spent grains contains 18.2% of cellulose and 20.4% of hemicellulose; and wherein a lactic acid concentration of the fermentation broth is not smaller than 50 g/L.

12. A method for efficiently producing lactic acid by fermenting brewers' spent grains, comprising the following steps:

adding a NaOH alkali solution with a concentration of 1.0 wt % into brewers' spent grains according to a solid-liquid weight ratio of 1:10, cooking at 120° C. for 15 min, carrying out a solid-liquid separation, obtaining and washing solid residues to a neutral state, and obtaining alkali-pretreated brewers' spent grains;

adding water to 20 g of the alkali-pretreated brewers' spent grains so as to adjust a solid content of a fermentation production system to 10%, adding cellulase into the alkali-pretreated brewers' spent grains according to an addition amount of 7.5 FPU/g, carrying out hydrolysis at 50° C. and pH of 5.0 for 30 hours, and obtaining a prehydrolyzed substrate;

inoculating the prehydrolyzed substrate with a lactic acid bacteria seed solution with a viable count of 3.7×10$^8$ CFU/mL according to an inoculation amount at a volume ratio of 10%, fermenting at 43° C. and pH of 6.0 for 84 hours, and obtaining a fermentation broth containing the lactic acid; and wherein a dry basis of the alkali-pretreated brewers' spent grains contains 18.2% of cellulose and 20.4% of hemicellulose; and wherein a lactic acid concentration of the fermentation broth is not smaller than 45 g/L.

\* \* \* \* \*